United States Patent [19]

Campbell et al.

[11] 4,243,666

[45] Jan. 6, 1981

[54] 4-AMINO-2-PIPERIDINO-QUINAZOLINES

[75] Inventors: Simon F. Campbell, Deal; John C. Danilewicz, Ash; Colin W. Greengrass, Sandwich; Rhona M. Plews, Canterbury, all of England

[73] Assignee: Pfizer Inc., New York, N.Y.

[21] Appl. No.: 38,509

[22] Filed: May 14, 1979

[30] Foreign Application Priority Data

May 18, 1978 [GB] United Kingdom ............ 20351/78

[51] Int. Cl.³ .................. A61K 31/505; C07D 401/04
[52] U.S. Cl. ............................... 424/248.54; 424/251; 544/122; 544/291
[58] Field of Search ............................ 544/291, 122; 424/248.54, 251

[56] References Cited

U.S. PATENT DOCUMENTS 3,511,836  5/1970  Hess ..................................... 544/291

Primary Examiner—Paul M. Coughlan, Jr.
Attorney, Agent, or Firm—Connolly and Hutz

[57] ABSTRACT

Regulators of the cardiovascular system and, in particular, in the treatment of hypertension having the formula

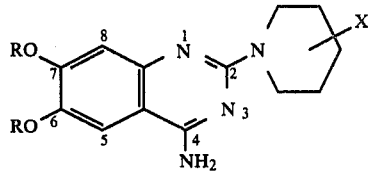

wherein
R is lower alkyl;
X, is a 3- or 4-position substituent and is $-(CH_2)_n CONR^1R^2$, $-O(CH_2)_n CONR^1R^2$ or

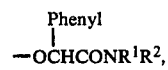

wherein
n is 0, 1 or 2;
$R^1$ is hydrogen or lower alkyl, and
$R^2$ is lower alkyl; lower alkenyl, lower alkynyl, phenyl, substituted phenyl, $C_3$-$C_7$ cycloalkyl; lower alkyl substituted by phenyl, substituted phenyl, $C_3$-$C_7$ cycloalkyl, halogen, trifluoromethyl, hydroxy, lower alkoxy, lower alkoxycarbonyl, phenoxy, substituted phenoxy or $-NR^3R^4$ wherein $R^3$ and $R^4$ each represent hydrogen, lower alkyl, lower alkanoyl or lower alkylsulfonyl; with the proviso that any O, N or halogen atom in $R^2$ is separated by at least 2 carbon atoms from the nitrogen atom to which $R^2$ is attached; or
$R^1$ and $R^2$ taken together with the nitrogen atom to which they are attached form a morpholino group optionally substituted by one or two lower alkyl groups, or a 1,2,3,4-tetrahydroisoquinolyl group optionally substituted on the benzene ring portion by one or two lower alkoxy groups;

the pharmaceutically acceptable bioprecursors therefor, and the pharmaceutically acceptable acid addition salts thereof.

10 Claims, No Drawings

4-AMINO-2-PIPERIDINO-QUINAZOLINES

BACKGROUND OF THE INVENTION

1. Field of the Invention

This invention relates to therapeutic agents which are novel derivatives of 4-amino-2-piperidinoquinazoline. Such compounds are useful as regulators of the cardiovascular system and, in particular, in the treatment of hypertension.

2. Description of the Prior Art

The therapeutic properties of a variety of quinazolines, including 4-amino-2-[(4-substituted)piperazin-1-yl]quinazolines are well known. U.S. Pat. No. 3,511,836 describes 4-amino-6,7-dialkoxy-2-[(4-substituted)-piperazin-1-yl]quinazolines wherein the 4-substituent is hydroxy, alkoxy or hydroxyalkyl. The products are valuable hypotensive agents.

SUMMARY OF THE INVENTION

The novel compounds according to the invention are those having the general formula:

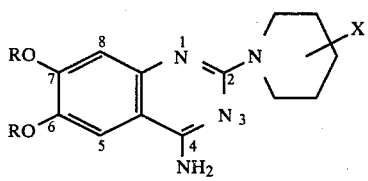

wherein
R is lower alkyl; and
X, which is attached to the 3-or 4- position of the piperidino group, is a group of the formula:
—$(CH_2)_n CONR^1 R^2$, —$O(CH_2)_n CONR^1 R^2$ or

wherein
n is 0, 1 or 2; and either
$R^1$ is hydrogen or lower alkyl, and
$R^2$ is lower alkyl, lower alkenyl, lower alkynyl, phenyl (as hereinafter defined);
$C_3$-$C_7$ cycloalkyl; or lower alkyl substituted by phenyl (as hereinafter defined), $C_3$-$C_7$ cycloalkyl, halogen, trifluoromethyl, hydroxy, lower alkoxy, lower alkoxycarbonyl, phenoxy, (as hereinafter defined) or a group of the formula —$NR^3 R^4$ wherein $R^3$ and $R^4$ each independently represent hydrogen, lower alkyl, lower alkanoyl, or lower alkylsulfonyl; with the proviso that any O, N or halogen atom in $R^2$ is separated by at least 2 carbon atoms from the nitrogen atom to which $R^2$ is attached; or
$R^1$ and $R^2$ taken together with the nitrogen atom to which they are attached form a morpholino group optionally substituted by one or two lower alkyl groups, or a 1,2,3,4-tetrahydroisoquinolyl group optionally substituted on the benzene ring portion by one or two lower alkoxy groups;
the pharmaceutically acceptable bioprecursors therefor, and the pharmaceutically acceptable acid addition salts thereof.

In this specification, "halogen" means fluorine, chlorine, bromine or iodine. The term "lower" applied to an alkyl, alkoxy, alkanoyl, alkenyl or alkynyl group indicates that such a group contains up to 6 carbon atoms, preferably up to 4 carbon atoms, and, where appropriate, such a group may be straight or branched chain.

By "phenyl" and "phenoxy" as used herein [including in -OCH (phenyl)$CONR^1 R^2$] is meant a phenyl or phenoxy group optionally substituted by one or two substituents selected from lower alkyl, lower alkoxy and halogen.

Pharmaceutically acceptable acid addiiton salts are those formed from acids which form non-toxic acid addition salts containing pharmaceutically acceptable anions, such as the hydrochloride, hydrobromide, sulphate or bisulphate, phosphate or acid phosphate, acetate, maleate, fumarate, lactate, tartrate, citrate, gluconate, saccharate or p-toluenesulfonate salts.

The compounds of the invention containing one or more asymmetric centres will exist as one or more pairs of enantiomers, and such pairs or individual isomers may be separable by physical methods, e.g. by fractional crystallisation of suitable salts. The invention includes the separated pairs as well as mixtures thereof, as racemic mixtures or as separated d- and l- optically active isomeric forms.

In one aspect X is other than

and $R^2$ is other than lower alkyl substituted by lower alkenyl, lower alkynyl or lower alkoxycarbonyl.

Preferred compounds of the invention have the formula (I) wherein:
R is methyl;
X is attached to the 4- position of the piperidino group and is a group of the formula:
(a) —$CONR^1 R^2$ in which $R^1$ is hydrogen, methyl or ethyl; and $R^2$ is $C_1$-$C_6$ alkyl; phenyl (as hereinbefore defined); $C_3$-$C_6$ cycloalkyl; or $C_1$ to $C_4$ alkyl substituted by phenyl (as hereinbefore defined), $C_3$-$C_6$ cycloalkyl, hydroxy, $C_1$ or $C_2$ alkoxy, —CH=$CH_2$,

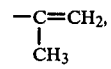

—C≡CH, ($C_1$ or $C_2$ alkoxy)carbonyl, phenoxy (as hereinbefore defined), —N($CH_3$)$_2$, —NHCOCH$_3$, —NHSO$_2$CH$_3$ or halogen; with the proviso that any O, N or halogen atom in $R^2$ is separated by at least 2 carbon atoms from the nitrogen atom to which $R^2$ is attached; or $R^1$ and $R^2$ taken together with the nitrogen atom to which they are attached form a morpholino group or a 1,2,3,4-tetrahydroisoquinolyl group optionally substituted on the benzene ring portion by one or two methoxy groups;
(b) —$CH_2 CONHR^2$ wherein $R^2$ is $C_1$-$C_6$ alkyl, benzyl, cyclopropylmethyl or —$CH_2 CH$=$CH_2$;
(c) —$CH_2 CH_2 CONHR^2$ wherein $R^2$ is $C_1$-$C_6$ alkyl or benzyl;
(d) —$O(CH_2)_n CONH(C_1$-$C_6$ alkyl) wherein n is 0 or 1; or
(e)

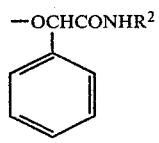

wherein $R^2$ is $C_1$–$C_6$ alkyl, benzyl or cyclopropylmethyl.

The most preferred compounds have the formula (I) in which each R is methyl and X is in the 4- position and represents a group of the formula:
—CONHC$_2$H$_5$
—CONH(CH$_2$)$_3$CH$_3$
—CONHCH$_2$.cyclopropyl
—CONH.benzyl
—CONH.CH$_2$CH=CH$_2$
—CH$_2$CONH(CH$_2$)$_2$CH$_3$ or
—CH$_2$CONHCH$_2$.cyclopropyl.

The term "pharmaceutically acceptable bioprecursor" used above requires some explanation. It is of course, common practice in pharmaceutical chemistry to overcome some undesirable physical or chemical property of a drug by converting the drug into a chemical derivative which does not suffer from that undesirable property, but which, upon administration to an animal or human being, is converted back to the parent drug.

For example, if the drug is not well absorbed when given to the animal or patient, by the oral route, it may be possible to convert the drug into a chemical derivative which is well absorbed and which in the serum or tissues is reconverted to the parent drug. Again, if a drug is unstable in solution, it may be possible to prepare a chemical derivative of the drug which is stable and may be administered in solution, but which is reconverted in the body to give the parent drug. The pharmaceutical chemist is well aware of the possibility of overcoming intrinsic deficiencies in a drug by chemical modifications which are only temporary and are reversible upon administration to the animal or patient.

For the purpose of this specification the term "pharmaceutically acceptable bioprecursor" of a compound of the formula (I) means a compound having a structural formula different from the compounds of the formula (I) but which nonetheless, upon administration to an animal or human being, is converted in the patient's body to a compound of the formula (I).

DETAILED DESCRIPTION OF THE INVENTION

The compounds of the invention can be prepared by a number of routes, including the following:

(1) The compounds can be prepared by reacting a quinazoline of the formula:

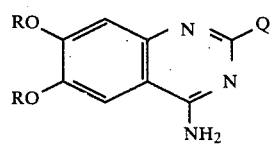

wherein R is as defined for formula (I), Q represents a facile leaving group such as chloro, bromo, iodo, lower alkoxy, (lower alkyl)thio or (lower alkyl)sulphonyl, with a piperidine of the formula:

wherein
X is as defined for formula (I).
Q is preferably chloro or bromo.

Typically the reaction is carried out in the presence of a tertiary organic amine base such as triethylamine or excess reagent of the formula (III), but this is not essential.

In a typical procedure, the reactants are heated together, e.g. under reflux, in an inert organic solvent, e.g. n-butanol, for periods of up to about 48 hours. The product can be isolated and purified by conventional procedures. Typically, the reaction mixture can be cooled, the solvent evaporated in vacuo, and the resulting solid shaken with e.g. chloroform and water. After filtration, the solid (or a salt thereof) can be recrystallised from a suitable solvent, e.g. ethanol, or may be purified by chromatography.

The intermediates of the formula (II) are in general known compounds or can be prepared by methods analogous to those of the prior art.

The intermediates of the formula (III) are either known compounds or can be prepared by conventional methods; the following routes are for example possible:

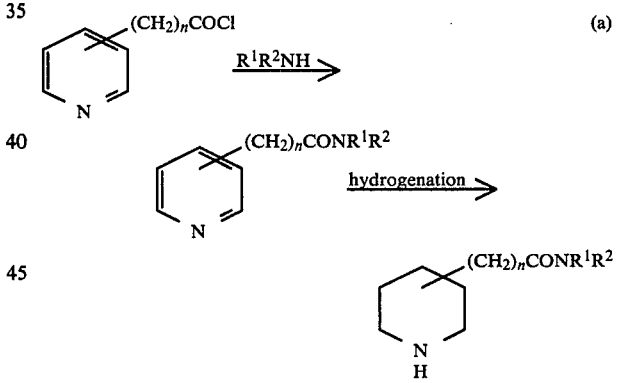

An acid bromide, "activated" ester or mixed anhydride could be used instead of the acid chloride;

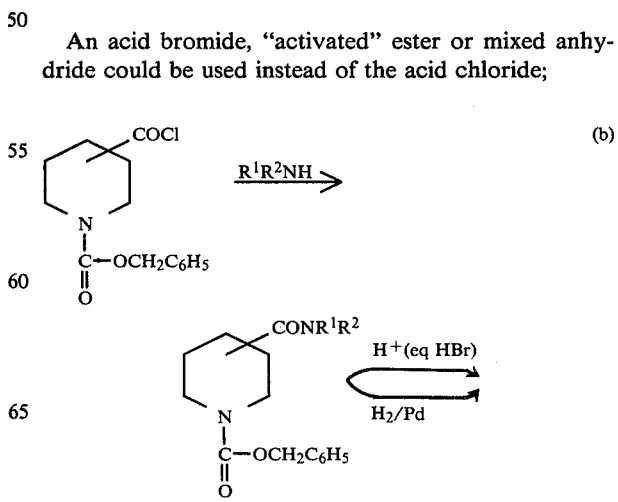

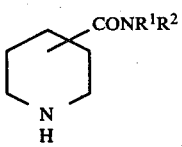

The starting 1-benzyloxycarbonylpiperidine-3- or 4-carboxylic acid chloride can be prepared similarly to the procedure of J. Org. Chem., 31, 2957 (1966).

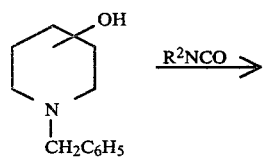 (c)

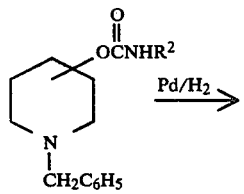

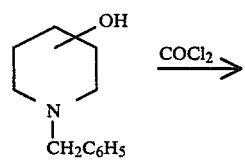 (d)

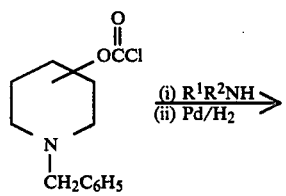

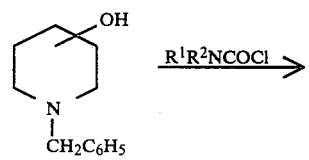 (e)

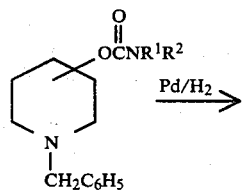

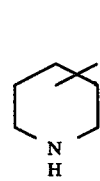 (f)

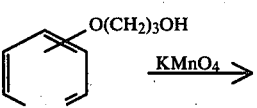

[Z = Cl, OCH$_3$ or OC$_2$H$_5$]

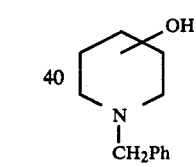

[n = 1 or 2]

The acid chlorides and esters of (f) are prepared by conventional procedures from the corresponding free acids. The pyridine acids in which n is 1 are either known compounds or may be prepared by procedures analogous to those of the prior art; those in which n is 2 can also be prepared by conventional procedures, e.g. from the corresponding alcohols:

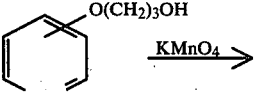 (g)

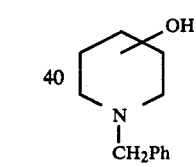

(2) The compounds of the formula (I) in which X is —(CH$_2$)$_n$CONR$^1$R$^2$ wherein n is 0, 1 or 2; —O(CH$_2$)$_n$CONR$^1$R$^2$ wherein n is 1 or 2, or —OCH(phenyl)-CONR$^1$R$^2$, R$^1$ and R$^2$ in all cases being as defined for formula (I), can be prepared by reacting an amine of the formula: R$^1$R$^2$NH with a compound of the formula:

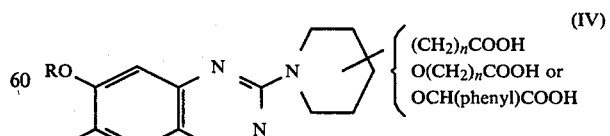 (IV)

wherein n is as defined above in this method and R is as defined for formula (I), or with its functional equivalent as an acylating agent, e.g. an acid chloride or bromide, "activated" ester, mixed anhydride or imidazolide of the compound of the formula (IV). If the free acid form (IV) is used, the reaction should generally be carried out in the presence of a dehydrating agent such as dicyclohexylcarbodiimide.

The acid chlorides and bromides can be prepared by conventional procedures, e.g. by reacting the free acid with, respectively, thionyl chloride or bromide.

The preferred "activated" esters are the succinimido and phthalimido esters, which again can be prepared by conventional procedures, e.g. by reacting the free acid with N-hydroxysuccinimide or N-hydroxyphthalimide in the presence of a dehydrating agent, e.g. dicyclohexylcarbodiimide.

Suitable mixed anhydrides have the formula:

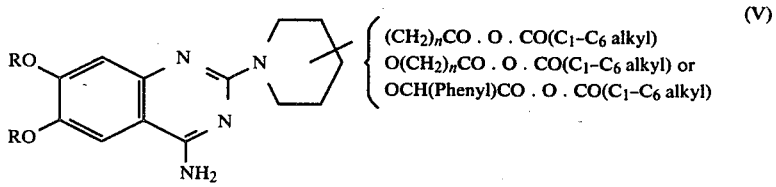

(V)

wherein R and n are as defined above in this method. These can be prepared by conventional procedures, e.g. by reacting the free acid with the appropriate alkanoyl chloride (e.g. pivaloyl chloride) in the presence of a base such as triethylamine.

(3) A compound in which $R^2$ is hydroxy-substituted lower alkyl can also be prepared by hydration of the corresponding compound in which $R^2$ is lower alkenyl-substituted lower alkyl, using conventional methods for such hydration.

The imidazolides of the formula:

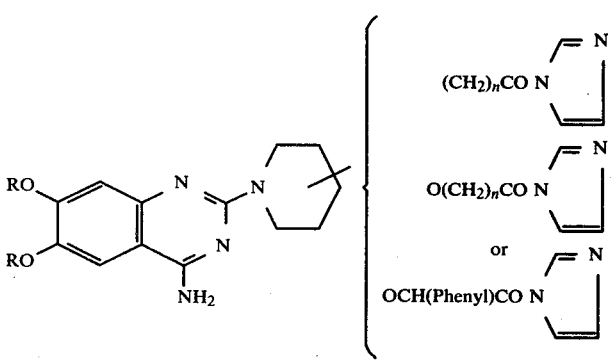

(VI)

wherein R and n are as defined above in this method can be prepared by the conventional technique of reacting the free acid (IV) in a suitable solvent, e.g. dimethylformamide, with N,N'-carbonyldiimidazole.

In a typical procedure, N,N'-carbonyldiimidazole can be added to a solution of the free acid (IV) in a suitable solvent, e.g. dimethylformamide, optionally in the presence of molecular sieves, at a temperature of 50°-100° C. After stirring the solution for 2-4 hours at this temperature, the amine of the formula $R^1R^2NH$ is added and the solution maintained in this temperature range for up to about 10 hours. After cooling, the molecular sieves can be removed by filtration, and washed well with chloroform. The chloroform washings and the filtrate can then be combined, washed with water, dried, and evaporated in vacuo to leave the crude product, which can be purified by conventional procedures.

An acid addition salt can be prepared by taking the crude product up in the minimum quantity of a suitable solvent, e.g. chloroform, and treating this solution with a solution of the appropriate acid in a suitable solvent, e.g. ethereal hydrogen chloride. The resulting precipitate of the acid addition salt can be filtered off, and if necessary, recrystallised from a suitable solvent, e.g. isopropanol/methanol.

The free acids of the formula (IV) can be prepared by conventional procedures, e.g. by reacting the appropriate 4-amino-6,7-di-(lower alkoxy)-2-chloroquinazoline with the appropriate substituted piperidine by a procedure similar to that of route (1) above.

The antihypertensive activity of the compounds of the invention is shown by their ability to lower the blood pressure of conscious spontaneously hypertensive rats and conscious renally hypertensive dogs, when administered orally at doses of up to 5 mg/kg.

The compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavouring or colouring agents. They can be injected parenterally, for example, intramuscularly, intravenously or subcutaneously. For parenteral administration, they are best used in the form of a sterile aqueous solution which may contain other solutes, for example, enough salt or glucose to make the solution isotonic.

Thus the invention also provides a pharmaceutical composition comprising a compound of the formula (I) or a pharmaceutically acceptable acid addition salt thereof, together with a pharmaceutically acceptable diluent or carrier.

The compounds of the invention can be administered to humans for the treatment of hypertension by either the oral or parenteral routes, typically in unit dosage form, and may be administered orally at dosage levels approximately within the range 0.5 to 50 mg/day for an average adult patient (70 kg), given in a single dose or up to 3 divided doses. Intravenous dosage levels would be expected to be about 1/5th to 1/10th of the daily oral dose. Thus for an average adult patient, individual oral doses in tablet or capsule form will be approximately in the range from 0.25 to 25 mg of the active compound. Variations will necessarily occur depending on the weight and condition of the subject being treated and the particular route of administration chosen as will be known to those skilled in the art.

The invention yet further provides a method of treating an animal, including a human being, having hypertension, which comprises administering to the animal an antihypertensive amount of a compound of the formula (I), a pharmaceutically acceptable acid addition salt thereof, or a pharmaceutical composition as defined above.

Also the invention provides a compound of the formula (I), a pharmaceutically acceptable acid addition salt thereof, or a pharmaceutical composition as defined above, for use in treating an animal, including a human being, having hypertension.

The following Examples, in which all temperatures are in °C., illustrate the invention:

EXAMPLE 1

Preparation of 4-Amino-6,7-dimethoxy-2-[4-(N-n-butylcarbamoyl)-piperidino]quinazoline hydrochloride

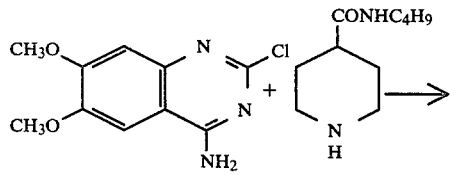

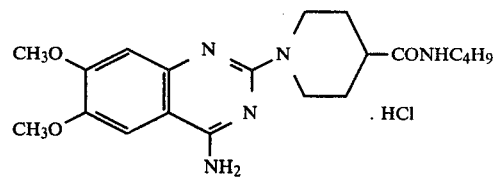

4-Amino-2-chloro-6,7-dimethoxyquinazoline (1.2 g), 4-(N-n-butylcarbamoyl)piperidine (1.01 g) and triethylamine (2.52 g) in n-butanol (105 ml) were heated under reflux for 24 hours. The mixture was then cooled, the solvent evaporated in vacuo, and the resultant solid shaken with chloroform and water. The solid product was collected by filtration, and recrystallised twice from ethanol to give 4-amino-6,7-dimethoxy-2-[4-(N-n-butylcarbamoyl)piperidino]quinazoline hydrochloride (0.57 g), m.p. 263°–264°.

Analysis %: Found: C, 56.8; H, 7.4; N, 16.5. Calculated for $C_{20}H_{29}N_5O_3 \cdot HCl$: C, 56.7; H, 7.1; N, 16.5.

EXAMPLES 2–18

The following quinazolines were prepared similarly to Example 1, starting from 4-amino-2-chloro-6,7-dimethoxyquinazoline and the appropriately substituted piperidine, and were isolated in the form indicated. In Examples 9 and 16, the crude product was purified by chromatography.

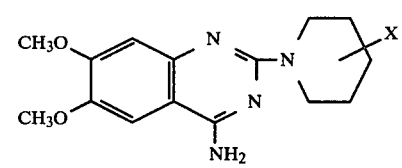

| Example No. | X | Position of attachment of X to piperidino group | Form Isolated and M.P. (°C.) | Analysis % (Theoretical in brackets) C | H | N |
|---|---|---|---|---|---|---|
| 2 | —CONH—⟨phenyl⟩ | 4- | hydrochloride, 263–266° | 59.4 (59.5 | 6.0 5.9 | 15.6 15.8) |
| 3 | —CONHCH₂—⟨phenyl⟩ | 4- | hydrochloride, 263–264° | 60.0 (60.3 | 6.0 6.1 | 15.1 15.3) |
| 4 | —CONHCH₂—⟨phenyl-OCH₃⟩ | 4- | hydrochloride, 269–270° | 59.5 (59.1 | 6.5 6.2 | 14.6 14.4) |

-continued

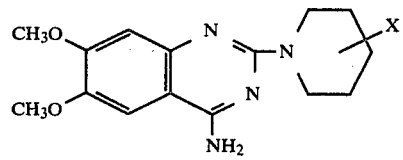

| Example No. | X | Position of attachment of X to piperidino group | Form Isolated and M.P. (°C.) | Analysis % (Theoretical in brackets) C | H | N |
|---|---|---|---|---|---|---|
| 5 | —CONHCH$_2$—(2,4-dichlorophenyl) | 4- | hydrochloride, 286–287° | 52.2 (52.4) | 4.9 (5.0) | 13.3 (13.3) |
| 6 | —CONHCH$_2$CH$_2$OH | 4- | hydrochloride, 279–281° | 52.9 (52.5) | 6.4 (6.4) | 17.6 (17.0) |
| 7 | —CONHCH$_2$CH$_2$OCH$_3$ | 4- | hydrochloride, 276–277° | 53.4 (53.6) | 6.5 (6.6) | 16.2 (16.4) |
| 8 | —CON(C$_2$H$_5$)$_2$ | 4- | hydrochloride hemihydrate, 283–284° | 55.3 (55.5) | 7.0 (7.2) | 15.9 (16.2) |
| 9 | —CON(C$_2$H$_5$)$_2$ | 3- | hydrochloride, 282° | 56.7 (56.6) | 7.1 (7.1) | 16.8 (16.5) |
| 10 | —CON(CH$_3$)—CH$_2$—phenyl | 4- | hydrochloride hydrate, 209–211° | 58.5 (58.8) | 6.2 (6.6) | 14.2 (14.2) |
| 11 | —CONH—CH(CH$_3$)—phenyl | 4- | hydrochloride, 251–252° | 60.5 (61.1) | 6.3 (6.4) | 14.6 (14.8) |
| 12 | —OC(O)NHC$_2$H$_5$ | 4- | hydrochloride, 275–276° | 51.9 (52.5) | 6.2 (6.4) | 16.9 (17.0) |
| 13 | —CON(1,2,3,4-tetrahydroisoquinoline) | 4- | hydrochloride hemihydrate 211–213° | 60.8 (60.9) | 6.1 (6.3) | 14.1 (14.2) |
| 14 | —CH$_2$CONH(CH$_2$)$_2$CH$_3$ | 4- | hydrochloride, 248–250° | 56.5 (56.7) | 7.0 (7.1) | 16.1 (16.5) |
| 15 | —C(O)NHCH$_2$CH$_2$CH$_2$CH$_3$ | 3- | hydrochloride hemihydrate 239–240° | 55.6 (55.5) | 7.0 (7.2) | 16.5 (16.2) |
| 16 | —OCH$_2$C(O)NHCH$_2$CH$_2$CH$_2$CH$_3$ | 4- | hydrochloride, 232–234° | 55.3 (55.6) | 7.1 (7.1) | 15.2 (15.4) |
| 17 | —OCH$_2$C(O)NHCH$_2$CH$_3$ | 4- | hydrochloride, 226–228° | 53.3 (53.6) | 6.7 (6.6) | 16.5 (16.4) |
| 18 | —C(O)NHCH$_2$—(2,4-dimethoxyphenyl) | 4- | hydrochloride hydrate 252–254° | 55.8 (56.0) | 6.1 (6.4) | 13.1 (13.1) |

EXAMPLE 19

Preparation of 4-Amino-6,7-dimethoxy-2-[4-(N-phenethylcarbamoyl)-piperazino]quinazoline hydrochloride

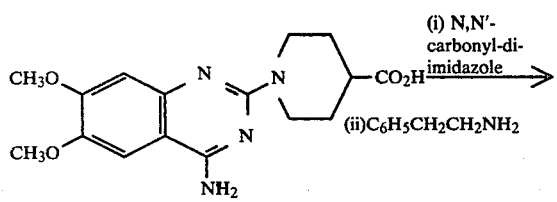

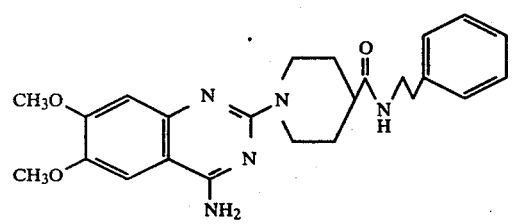

N,N'-carbonyldiimidazole (2.0 g) was added to 4-amino-2-(4-carboxypiperidino)-6,7-dimethoxyquinazoline (2.0 g) in dimethylformamide (100 ml) in the presence of 3A molecular sieves at 70°. The solution was stirred at 70° for 2 hours, then 2-phenylethylamine (1.0 g) was added and the reaction maintained at 70° for a further 5 hours. The mixture was then allowed to stand at room temperature overnight, then stirred at 70° for 3 hours. After cooling, the molecular sieves were removed by filtration, and washed well with chloroform. The filtrate and the chloroform washings were combined and the resulting solution was washed with water, dried ($Na_2SO_4$) and evaporated in vacuo. The resulting residue was taken up in the minimum volume of chloroform, treated with ethereal hydrogen chloride, the solid product collected, washed with ether, and crystallised from isopropanol/methanol to give 4-amino-6,7-dimethoxy-2-[4-(N-phenethylcarbamoyl)piperidino]quinazoline hydrochloride (0.81 g), m.p. 284°–285°.

Analysis %: Found: C, 61.0; H, 6.5; N, 14.5. Calculated for $C_{24}H_{29}N_5O_3.HCl$: C, 61.1; H, 6.4; N, 14.8.

EXAMPLES 20–43

The following compounds were prepared similarly to Example 19, starting from the appropriate carboxy-containing quinazoline, N,N'-carbonyl-di-imidazole, and the appropriate amine of the formula $R^1R^2NH$. In Examples 20 to 22, 25, 27 to 30, 34, and 40–43, the crude product was purified by chromatography on silica eluting with a mixture of chloroform and methanol.

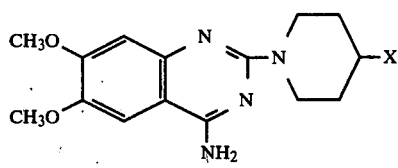

| Example No. | X | Form Isolated and m.p. (°C.) | Analysis % (Theoretical in brackets) | | |
|---|---|---|---|---|---|
| | | | C | H | N |
| 20 | —$CONHC_2H_5$ | hydrochloride hemihydrate, 287–288° | 53.7 (53.4) | 6.7 (6.7) | 17.4 (17.3) |
| 21 | —$CONHCH(CH_3)_2$ | hydrochloride hemihydrate, 281–282° | 54.6 (54.5) | 6.9 (7.0) | 16.9 (16.7) |
| 22 | —CONH . cyclopentyl | hydrochloride hydrate, 263–264° | 55.5 (55.6) | 6.8 (7.1) | 15.4 (15.4) |
| 23 | —CON⟨O⟩ (morpholino) | hydrochloride, >300° | 54.6 (54.9) | 6.3 (6.4) | 16.0 (16.0) |
| 24 | —$CONHCH_2CH_2N(CH_3)_2$ | dihydrochloride 1½ hydrate, 244–245° | 47.5 (48.0) | 6.4 (6.7) | 16.5 (16.8) |
| 25 | —$CH_2CH_2C(O)NHCH_2CH_3$ | hydrochloride, 242–243° | 56.7 (56.7) | 7.2 (7.1) | 16.9 (16.5) |
| 26 | —$CH_2CH_2C(O)NHCH_2$—C$_6$H$_5$ | hydrochloride, 238–239° | 61.8 (61.8) | 6.3 (6.6) | 14.1 (14.4) |
| 27 | —$CH_2CH_2C(O)NH(CH_2)_3CH_3$ | hydrochloride, 219–220° | 58.1 (58.5) | 7.5 (7.6) | 15.6 (15.5) |
| 28 | —$CH_2C(O)NHCH_2CH_3$ | hydrochloride hemihydrate, 238–239° | 54.6 (54.5) | 7.0 (7.0) | 16.5 (16.7) |
| 29 | —$CH_2C(O)NHCH_2$—C$_6$H$_5$ | hydrochloride hemihydrate, 254–255° | 59.6 (59.9) | 6.3 (6.5) | 14.8 (14.6) |

-continued

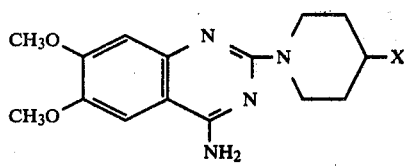

| Example No. | X | Form Isolated and m.p. (°C.) | Analysis % (Theoretical in brackets) C | H | N |
|---|---|---|---|---|---|
| 30 | -CH₂C(O)NHCH₂-cyclopropyl | hydrochloride hemihydrate, 247-249° | 56.6 (56.7) | 7.0 (7.0) | 15.6 (15.7) |
| 31 | -C(O)NH(CH₂)₃NHC(O)CH₃ | hydrochloride hemihydrate, 256-257° | 53.3 (53.0) | 6.6 (6.8) | 18.0 (17.7) |
| 32 | -C(O)NHCH₂CH₂O-phenyl | free base, 210-212° | 63.4 (63.8) | 6.7 (6.5) | 15.3 (15.5) |
| 33 | -C(O)NH(CH₂)₂NHC(O)CH₃ | free base hemihydrate, 252-255° | 56.8 (56.5) | 6.7 (6.9) | 19.5 (19.8) |
| 34 | -CH₂C(O)NHCH₂CH=CH₂ | hydrochloride hemihydrate, 239-241° | 56.0 (55.7) | 6.6 (6.8) | 16.7 (16.3) |
| 35 | -C(O)NHCH₂C(O)OC₂H₅ | hydrochloride hemihydrate, 250-251° | 51.8 (51.9) | 6.0 (6.3) | 15.2 (15.1) |
| 36 | -C(O)NHCH₂CH₂N(H)SO₂CH₃ | hydrochloride hemihydrate, 256-258° | 59.6 (59.8) | 6.5 (6.4) | 14.2 (13.9) |
| 37 | -CONHCH₂-cyclohexyl | hydrochloride hemihydrate, 242-243° | 58.3 (58.4) | 7.3 (7.5) | 14.6 (14.8) |
| 38 | -OCH(phenyl)-CONHC₂H₅ | hydrochloride, 256-258° | 59.6 (59.8) | 6.5 (6.4) | 14.2 (13.9) |
| 39 | -OCH(phenyl)CONHCH₂·Phenyl | hydrochloride hydrate, 175-180° | 61.2 (61.9) | 6.1 (6.2) | 11.8 (12.0) |
| 40 | -OCH(phenyl)CONH(CH₂)₃CH₃ | hydrochloride hemihydrate, 195-198° | 60.1 (60.2) | 6.7 (6.9) | 13.0 (13.0) |
| 41 | -OCH(phenyl)CONHCH₂-cyclopropyl | hydrochloride, 210-213° | 61.0 (61.4) | 6.6 (6.5) | 13.7 (13.3) |
| 42 | -CONHCH₂CH₂CH₂Cl | free base hydrate, 251-253° | 53.6 (53.6) | 6.4 (6.6) | 16.7 (16.4) |
| 43 | -CONHCH₂CH₂OC₂H₅ | hydrochloride hemihydrate, 255-258° | 53.6 (53.5) | 6.8 (7.0) | 15.8 (15.6) |

EXAMPLE 44

Preparation of
4-Amino-2-[4-(N-allylcarbamoyl)piperidino]-6,7-dimethoxyquinazoline hydrochloride

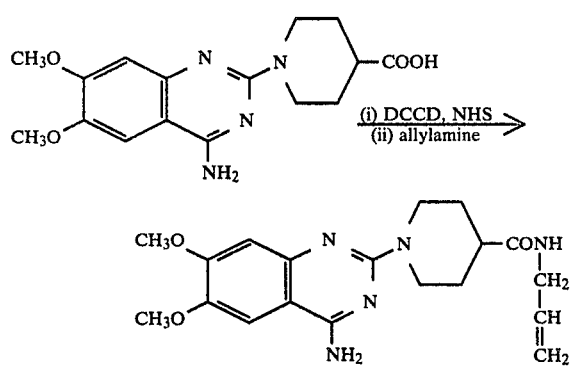

4-Amino-2-[4-carboxypiperidino]-6,7-dimethoxyquinazoline (2.3 g), dicyclohexylcarbodiimide (DCCD) (1.4 g) and N-hydroxysuccinimide (NHS) (0.8 g) were stirred together in dry dimethylformamide (DMF) for 2 hours at 60°. Allylamine (0.4 g) was then added to the resultant suspension and heating at 60° was continued for a further 6 hours. 5 N Hydrochloric acid (50 ml) was then added to the cooled mixture, followed by the addition of chloroform (50 ml). The mixture was shaken and separated. The aqueous phase was basified to pH 12 with 5 N sodium hydroxide solution and extracted with chloroform (2×50 ml). The chloroform extract was dried (MgSO₄) and evaporated in vacuo to give a yellow gum (1.4 g) which was taken up in the minimum quantity of isopropanol and treated with dry hydrogen chloride gas to slight excess. Recrystallisation of the product from a mixture of ethyl acetate-methanol gave pure 4-amino-2-[4-(N-allylcarbamoyl)piperidino]-6,7-dimethoxyquinazoline hydrochloride hemihydrate (0.6 g), m.p. 277°.

Analysis %: Found: C, 54.9; H, 6.5; N, 16.9. $C_{19}H_{25}N_5O_3 \cdot HCl \cdot \tfrac{1}{2}H_2O$ requires: C, 54.6; H, 6.6; N, 16.8.

EXAMPLES 45 TO 55

The following compounds were prepared similarly to the previous Example, starting from the appropriate carboxy-containing piperidinoquinazoline, N-hydroxysuccinimide, dicyclohexylcarbodiimide and the appropriate amine of the formula $R^1R^2NH$.

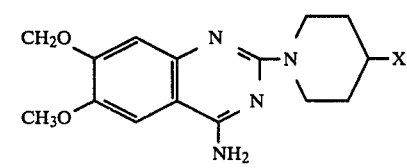

| Example No. | X | Form Isolated and m.p. (°C.) | Analysis % (Theoretical in brackets) | | |
|---|---|---|---|---|---|
| | | | C | H | N |
| 45 | —CNHCH₂—▷ (C=O) | hydrochloride hemihydrate, 270–272° | 55.5 (55.7 | 6.6 6.8 | 16.3 16.3) |
| 46 | —CNHCH₂C(=CH₂)CH₃ (C=O) | oxalate monohydrate, 242° | 53.5 (53.5 | 5.8 6.3 | 14.4 14.2) |
| 47 | —CNHCH₂C≡CH (C=O) | oxalate ¼H₂O, 249–250° | 54.3 (54.4 | 5.5 5.5 | 14.7 15.1) |
| 48 | —CNHCH₂—C₆H₄—OCH₃ (C=O) | hydrochloride monohydrate, 260° | 57.4 (57.0 | 6.2 6.4 | 13.6 13.8) |
| 49 | —CNHCH₂—C₆H₄—OC₂H₅ (C=O) | hydrochloride monohydrate, 241–242° | 57.8 (57.7 | 6.3 6.6 | 13.8 13.5) |
| 50 | —CNHCH₂—C₆H₃(OCH₃)₂ (C=O) | hydrochloride sesquihydrate 250–251° (softens at 180°) | 54.9 (55.1 | 5.9 6.5 | 13.0 12.9) |
| 51 | —CNHCH₂—C₆H₄—CH₃ (C=O) | hydrochloride dihydrate, 250–251° | 56.8 (56.7 | 6.2 6.8 | 13.8 13.8) |
| 52 | —CNHCH₂—C₆H₄—Cl (C=O) | hydrochloride sesquihydrate, 215–216° | 53.2 (53.2 | 5.9 5.8 | 13.6 13.5) |
| 53 | —CNHCH₂—C₆H₄—CH₃ (ortho) (C=O) | hydrochloride hemihydrate, 290–292° | 59.6 (59.9 | 6.6 6.5 | 14.7 14.6) |

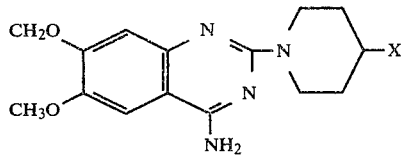

| Example No. | X | Form Isolated and m.p. (°C.) | Analysis % (Theoretical in brackets) | | |
|---|---|---|---|---|---|
| | | | C | H | N |
| 54 | —N with CH2CH2-bridged dimethoxyphenyl ring, OCH3, OCH3) | hydrochloride dihydrate, 210–212° | 56.3 (55.9 | 6.2 6.6 | 12.3 12.1) |
| 55 | —CNHCH2—(phenyl)—OCH3, OCH3 (with O=C) | hydrochloride hemihydrate 266–267° | 57.1 (57.0 | 6.3 6.3 | 13.6 13.3) |

EXAMPLE 56

Preparation of 4-Amino-6,7-dimethoxy-2-[4-(N-{2-methyl-2-hydroxypropyl}carbamoyl)pyperidino]quinazoline hydrochloride monohydrate.

4-Amino-6,7-dimethoxy-2-[4-(N-{2-methylallyl}carbamoyl)piperidino]quinazoline (2.0 g) was dissolved in 50% aqueous sulphuric acid (100 ml) and the solution was allowed to stand at ambient temperature for 24 hours. The mixture was then cooled by ice-water and basified to pH 8.0 by the addition of concentrated (0.880 density) ammonia, after which it was evaporated to dryness. The residue was suspended in hot ethanol (200 ml), filtered to remove inorganic salts and the filtrate concentrated in vacuo to give a white solid (1.6 g). The solid was dissolved in methanol (10 ml) and treated with a slight excess of ethereal hydrochloric acid. Recrystallisation of the resultant solid from ethylacetate/methanol gave 4-amino-6,7 dimethoxy-2-[4-(N{2-methyl-2-hydroxypropyl}carbamoyl)piperidino]quinazoline hydrochloride monohydrate (0.6 g), m.p. 232°–4°.

Analysis, %: Found: C, 52.4; H, 6.8; N, 15.1. Calculated for $C_{20}H_{29}N_5O_4.HCl.H_2O$: C, 52.5; H, 7.0; N, 15.3.

EXAMPLE 57

Preparation of 4-Amino-2-[4-(N-n-butyl-carbamoylmethyl)-piperidino]-6,7-dimethoxyquinazoline hydrochloride 4-Amino-2-[4-carboxymethylpiperidino]-6,7-dimethoxyquinazoline (3.0 g), N,N'-dicyclohexylcarbodiimide (1.83 g) and N-hydroxysuccinimide (1.04 g) in dry DMF (50 ml) were stirred at 70° for 2 hours. n-Butylamine (10 ml) was then added and the solution stirred at 50° for 4 hours. The cooled solution was filtered, the filtrate treated with hydrochloric acid solution (5 N, 50 ml) and extracted with chloroform (3×50 ml). The chloroform extract was dried (Na2SO4) and the solvent evaporated in vacuo to give an oil which was taken up in hydrochloric acid (10 ml, 2 N) and shaken with ethyl acetate. The aqueous phase was separated, adjusted to pH 11 with sodium hydroxide solution and extracted with chloroform (3×20 ml). The chloroform extract was dried and the solvent evaporated in vacuo. The residue was treated with dioxan, filtered and the filtrate evaporated in vacuo. The product was chromatographed on silica (100 g) eluting with chloroform followed by chloroform/methanol (30:1). Fractions containing the product were combined, concentrated and the residue in chloroform converted to the hydrochloride salt by treatment with ethereal hydrogen chloride. Recrystallisation from methanol/dioxan gave 4-amino-2-[4-(N-n-butylcarbamoylmethyl)piperidino]-6,7-dimethoxyquinazoline hydrochloride hemihydrate, (0.25 g), m.p. 238°–239°.

Analysis %: Found: C, 56.5; H, 7.3; N, 15.4. Calculated for $C_{21}H_{31}N_5O_3.HCl.\tfrac{1}{2}H_2O$: C, 56.4; H, 7.4; N, 15.7.

EXAMPLE 58

Preparation of 4-Amino-6,7-dimethoxy-2-[4-(N-[2,2-dimethylpropyl]-carbamoylmethyl)piperidino]quinazoline hydrochloride 4-Amino-2-[4-(carboxymethyl)piperidino]-6,7-dimethoxyquinazoline (3.0 g), N,N'-dicyclohexylcarbodiimide (1.83 g) and N-hydroxysuccinimide (1.04 g) in dry DMF were stirred at 70° for 2½ hours. Then 2,2-dimethylpropylamine (0.78 g) was added and the mixture stirred for 4 hours at 50°. The cooled solution was filtered and the filtrate concentrated in vacuo. The residue was taken up in chloroform (50 ml), extracted with sodium bicarbonate solution, the organic layer dried (Na2SO4) and the solvent evaporated in vacuo. The residue was chromatographed on silica (120 g) eluting with chloroform followed by chloroform/methanol 20:1. Fractions containing the product were combined, concentrated and the residue in chloroform converted to the hydrochloride salt by treatment with ethereal hydrogen chloride. Recrystallisation of the solid from methanol/dioxan followed by methanol/acetonitrile gave 4-amino-6,7-dimethoxy-2-[4-(N-{2,2-dimethylpropyl}carbamoylmethyl)piperidino]quinazoline, hydrochloride hemihydrate (0.45 g), m.p. 228°–231°.

Analysis %: Found: C, 57.3; H, 7.8; N, 15.3. Calculated for $C_{22}H_{33}N_5O_3.HCl.\tfrac{1}{2}H_2O$: C, 57.3; H, 7.7; N, 15.2.

EXAMPLE 59

Preparation of 4-Amino-6,7-dimethoxy-2-[4-(N-n-propylcarbamoyl)-piperidino]quinazoline hydrochloride This was prepared similarly to the previous Example from 4-amino-2-(4-carboxypiperidino)-6,7-dimethoxyquinazoline and n-propylamine but without chromatographic purification. The hydrochloride hemihydrate was recrystallised from methanol/isopropanol followed by ethanol and had an m.p. of 263°–264°.

Analysis %: Found: C, 54.4; H, 6.6; N, 16.8. Calculated for $C_{19}H_{27}N_5O_3.HCl.\frac{1}{2}H_2O$: C, 54.5; H, 7.0; N, 16.7.

The following Preparations, in which all temperatures are given in °C., illustrate the preparation of certain of the starting materials used in the previous Examples:

PREPARATION A

Preparation of 4-(N-phenylcarbamoyl)piperidine 4-(N-phenylcarbamoyl)pyridine [75.0 g, prepared as in Chem. Abs., 2013h (1958)] was hydrogenated in acetic acid (800 ml) using a platinum oxide catalyst at 50 p.s.i./30°. The catalyst was then removed by filtration, the solution evaporated, the residue basified to about pH 12 with sodium hydroxide, extracted with chloroform, and the organic extract discarded. The aqueous phase was evaporated to dryness, the residue boiled with chloroform, filtered and evaporated to leave 4-(N-phenylcarbamoyl)piperidine (17.0 g), m.p. 121°–127°. The hydrochloride salt, m.p. 231°–233°, was prepared in isopropanol from the free base and hydrogen chloride, and was recrystallised from isopropanol/ethyl acetate.

Analysis %: Found: C, 60.1; H, 7.2; N, 11.7. Calculated for $C_{12}H_{16}N_2O.HCl$: C, 59.9; H, 7.1; N, 11.6.

PREPARATION B

Preparation of 4-(N-n-butylcarbamoyl)piperidine

Isonicotinoyl chloride (100.0 g) was added over 1 hour to a solution of n-butylamine (51.6 g) in toluene (600 ml) at 0°. The mixture was allowed to stand overnight, heated on a steam bath for $\frac{1}{2}$ hour, then water was added. The aqueous layer was separated, basified to about pH 12 (NaOH), and extracted with ethyl acetate (2 times). The combined organic extracts were dried ($MgSO_4$), evaporated and the resulting residue (36.0 g) dissolved in acetic acid (400 ml) and hydrogenated at 50 p.s.i./30° in the presence of platinum oxide. The catalyst was removed by filtration, the solution evaporated to dryness, the residue basified to about pH 12 ($Na_2CO_3$), and extracted with chloroform. The chloroform extracts were dried ($Na_2SO_4$) and evaporated to give 4-(N-n-butylcarbamoyl)piperidine, (18.7 g), m.p. 75°–79°. The oxalate salt was prepared in isopropanol from the free base and oxalic acid and was recrystallised from isopropanol/ethyl acetate, m.p. 143°–144°.

Analysis %: Found: C, 52.9; H, 8.0; N, 10.3. Calculated for $C_{10}H_{20}N_2O.C_2H_2O_4$: C, 52.5; H, 8.1; N, 10.2.

PREPARATION C

Preparation of 4-(N-2,4-dichlorobenzylcarbamoyl)piperidine

A solution of 1-benzyloxycarbonylpiperidine-4-carboxylic acid chloride [4.6 g, prepared as in J. Org. Chem. 31, 2957 (1966)] in chloroform (25 ml) was added dropwise to a cooled (ice/water) solution of 2,4-dichlorobenzylamine (3.87 g) and triethylamine (2.2 g) in chloroform (100 ml). After the addition was complete, the solution was left at room temperature for 1 hour, washed with water, dried ($Na_2SO_4$) and evaporated. The resulting solid residue was crystallised from toluene/methanol to give 1-benzyloxycarbonyl-4-(N-2,4-dichlorobenzylcarbamoyl)piperidine (7.04 g), m.p. 144°–145°.

Analysis %: Found: C, 60.0; H, 5.2; N, 6.8. Calculated for $C_{21}H_{22}N_2O_3Cl_2$: C, 59.9; H, 5.3; N, 6.7.

A cooled (ice/water) and stirred solution of the above product (6.5 g) in acetic acid (25 ml) was slowly treated with a saturated solution of hydrogen bromide in acetic acid (25 ml). The reaction mixture was stirred at 20° for 1 hour when a precipitate formed. Dry ether (100 ml) was then added, the solid product collected, and washed with ether to give 4-(N-2,4-dichlorobenzylcarbamoyl)piperidine hydrobromide (3.4 g), m.p. 171°–173°, with i.r. and n.m.r. spectra consistent with this structure.

The product was used in Example 5 without further purification.

PREPARATION D

Preparation of 4-(N-2-methoxybenzylcarbamoyl)piperidine

The above compound was prepared similarly to Preparation C starting from 1-benzyloxycarbonyl-piperidine-4-carboxylic acid chloride and 2-methoxybenzylamine and had an m.p. of 139°–140°.

Analysis %: Found: C, 67.3; H, 8.1; N, 11.0. Calculated for $C_{14}H_{20}N_2O_2$: C, 67.7; H, 8.1; N, 11.3.

PREPARATION E

Preparation of 4-(N-methyl-N-benzylcarbamoyl)piperidine

This compound was prepared similarly to Preparation C starting from 1-benzyloxycarbonylpiperidine-4-carboxylic acid chloride and N-methylbenzylamine, and was used directly in Example 10. This intermediate was characterised as the hydrochloride salt, m.p. 175°–176°.

Analysis %: Found: C, 62.4; H, 7.7; N, 10.1. Calculated for $C_{14}H_{20}N_2O.HCl$: C, 62.6; H, 7.9; N, 10.4.

PREPARATION F

Preparation of 4-(1,2,3,4-Tetrahydroisoquinol-2-ylcarbonyl)piperidine

This compound was prepared similarly to Preparation C, starting from 1-benzyloxycarbonylpiperidine-4-carboxylic acid chloride and 1,2,3,4-tetrahydroisoquinoline, and was used directly in Example 13. This intermediate was characterised as the hydrochloride salt, m.p. 245°–247°.

Analysis %: Found: C, 63.6; H, 7.6; N, 9.9. Calculated for $C_{14}H_{20}N_2O.HCl$: C, 64.2; H, 7.6; N, 10.0.

PREPARATION G

Preparation of 4-[N-(2-methoxyethyl)carbamoyl]piperidine

1-Benzyloxycarbonyl-4-[N-(2-methoxyethyl)carbamoyl]piperidine [5.76 g, m.p. 85°–86°, Analysis %: C, 63.9; H, 7.5; N, 8.4; Calculated: C, 63.7; H, 7.6; N, 8.8; prepared similarly to Preparation C but using toluene in place of chloroform and starting from 1-benzyloxycarbonylpiperidine-4-carboxylic acid chloride and 2-methoxyethylamine] in ethanol (75 ml) was hydrogenated over 5% palladium on charcoal at 50 p.s.i./50°. The catalyst was removed by filtration, and the filtrate evaporated to give 4-[N-(2-methoxyethyl)carbamoyl]piperidine as an oil which solidified on standing. I.r. and n.m.r. spectra were consistent with this structure and the product was used in Example 7 without further purification.

PREPARATION H

Preparation of 4-[N-(2-hydroxyethyl)carbamoyl]piperidine

1-Benzyloxycarbonyl-4-[N-(2-hydroxyethyl)carbamoyl]piperidine [6.24 g, m.p. 107°–108°, Found: C, 62.8; H, 7.2; N, 9.0; Calculated: C, 62.7; H, 7.2; N, 9.1; prepared similarly to Preparation C but starting from 1-benzyloxycarbonylpiperidine-4-carboxylic acid chloride and 2-hydroxyethylamine] was hydrogenated as in Preparation G to give 4-[N-(2-hydroxyethyl)carbamoyl]piperidine. The i.r. and n.m.r. spectra were consistent with this structure and the product was used in Example 6 without further purification.

PREPARATION I

Preparation of 4-[N-(α-methylbenzyl)carbamoyl]piperidine

1-Benzyloxycarbonyl-4-[N-(α-methylbenzyl)carbamoyl]piperidine [5.5 g, m.p. 136°, prepared as in Preparation C starting from 1-benzyloxycarbonylpiperidine-4-carboxylic acid chloride and α-methylbenzylamine; Analysis %: Found: C, 72.2; H, 7.1; N, 7.5; Calculated for $C_{22}H_{26}N_2O_3$: C, 72.1; H, 7.2; N, 7.7] was hydrogenated as in Preparation G and the crude product was used in Example 11 without further purification.

PREPARATION J

Preparation of 4-Amino-2-(4-carboxypiperidino)-6,7-dimethoxyquinazoline monohydrate The above was prepared similarly to Example 1, starting from 4-amino-2-chloro-6,7-dimethoxyquinazoline and 4-carboxypiperidine and had an m.p. of 295°.

Analysis %: Found: C, 54.9; H, 6.0; N, 16.1. Calculated for $C_{16}H_{20}N_4O_4.H_2O$: C, 54.8; H, 6.4; N, 16.0.

PREPARATION K

Preparation of 4-(N-Ethylcarbamoyloxy)piperidine

1-Benzyl-4-piperidinol (293.4 g), ethyl isocyanate (120 g) and 1,2-dichloroethane (1467 ml) were heated and stirred together under reflux for 7 hours. A further 10.9 g of ethyl isocyanate was then added and reflux was continued for another 6 hours. After cooling and standing for 36 hours at room temperature, the reaction had not proceeded to completion and so a further 33 g of ethyl isocyanate was added and heating under reflux continued for a further 6 hours. The mixture was cooled, poured into water (2000 ml) and stirred for 1½ hours, after which the organic layer was separated, washed with saturated sodium bicarbonate solution (2000 ml) and water (2000 ml).

The combined aqueous phases were further extracted with dichloroethane (150 ml) and the bulked organic phases were dried (MgSO4) and evaporated in vacuo to give a crude product which was stirred with boiling hexane, cooled, and filtered to give 1-benzyl-4-(N-ethylcarbamoyloxy)piperidine (354.4 g), m.p. 96°–98° C.

This product (118 g) in industrial methylated spirit (826 ml) was hydrogenated at 50°/50 p.s.i. over 5% palladium on charcoal catalyst (12 g) until uptake of hydrogen ceased. The catalyst was then removed by filtration, the filtrate evaporated in vacuo, and the resulting residue was recrystallised from a mixture of hexane (450 ml) and ethyl acetate (112 ml) to give 4-(N-ethylcarbamoyloxy)piperidine (208.1 g), m.p. 85°–87°, used directly in Example 12.

PREPARATION L

A. Preparation of 2-(1-benzylpiperidin-4-oxy)acetic acid, hydrochloride

1-Benzyl-4-hydroxypiperidine (10 g) in dry DMF (50 ml) was added dropwise to a stirred suspension of sodium hydride (5 g, 50% dispersion in mineral oil) in dry DMF (50 ml) at 20° under an atmosphere of nitrogen. The suspension was stirred at 20° for 4 hours, then 2-chloroacetic acid (4.95 g) in DMF (50 ml) was added slowly in two equal portions with a 2 hour interval between each. The resulting thick slurry was stirred at 20° for 24 hours. Isopropanol (75 ml) was added and the slurry was acidified to pH 6 with 2 N hydrochloric acid then concentrated in vacuo. The aqueous residue was adjusted to pH 10 with sodium hydroxide solution and extracted with chloroform (3×100 ml). The aqueous layer was separated, acidified to pH 3 with 2 N hydrochloric acid and extracted with chloroform (3×100 ml). The organic extracts were again discarded and the aqueous phase was concentrated to half volume, filtered and the filtrate evaporated in vacuo to give 2-(1-benzylpiperidin-4-oxy)acetic acid, hydrochloride (3 g), characterised by n.m.r.

B. Preparation of N-n-butyl-2-(piperidin-4-oxy)acetamide, hydrochloride 2-(1-Benzylpiperidin-4-oxy)acetic acid, hydrochloride, (7.0 g) and thionyl chloride (5 ml) in dry chloroform (100 ml) were heated under reflux for 2½ hours. The solvent was evaporated in vacuo and the resulting acid chloride taken up in chloroform (50 ml) and added dropwise to a solution of n-butylamine (5 ml) in chloroform (50 ml) with stirring at 0°. The solution was stirred at 0° for 4 hours then left at room temperature overnight. The chloroform solution was washed with water (3×50 ml), sodium hydroxide solution (3×50 ml, 2 N) and hydrochloric acid solution (3×50 ml, 2 N). The aqueous acid solution was basified to pH 12 and extracted with chloroform (3×100 ml). The chloroform extract was dried and the solvent evaporated in vacuo. The residue in ether was treated with ethereal hydrogen chloride, the resulting solid collected, washed with ether and dried to give N-n-butyl-2-(1-benzylpiperidin-4-oxy)acetamide, hydrochloride (3.5 g) identified by n.m.r. spectroscopy.

This product (3 g) in ethanol (100 ml) was hydrogenated over 5% palladium on charcoal (Engelhardt special debenzylation catalyst) at 50°/50 p.s.i. The catalyst was removed by filtration and the solvent evaporated in vacuo. The residue was triturated with ether and the white solid filtered off to give N-n-butyl-2-(piperidin-4-oxy) acetamide, hydrochloride, (1.7 g). A sample was recrystallised from isopropanol/diethyl ether then ethyl acetate and had an m.p. of 145°–146°.

Analysis %: Found: C, 52.3; H, 9.2; N, 10.9. Calculated for $C_{11}H_{22}N_2O_2.HCl$: C, 52.7; H, 9.3; N, 11.2.

PREPARATION M

Preparation of N-ethyl-2-(piperidin-4-oxy)acetamide 2-(1-Benzylpiperidin-4-oxy)acetic acid, hydrochloride, prepared similarly to Preparation L Part A, was converted to its methyl ester by refluxing in methanol plus concentrated hydrochloric acid. Methyl 2-(1-benzylpiperidin-4-oxy)acetate (10 g) and ethylamine (50 ml) with 3 A molecular sieves were heated in a bomb at 120° for 6 hours. The solvent was then evaporated in vacuo, the residue triturated with ether, filtered and the filtrate evaporated to give N-ethyl-2-(1-benzylpiperidin-4-oxy)acetamide (7.7 g) as an oil. This product (7.0 g) in ethanol (150 ml) was hydrogenated over 5% palladium on charcoal (Engelhardt special debenzylation catalyst) at 50° and 50 p.s.i.

The catalyst was removed by filtration, the filtrate evaporated and the residue taken up in toluene and evaporated in vacuo to give N-ethyl-2-(piperidin-4-oxy)acetamide (4.8 g) as an oil. A sample in ether was converted to the hydrochloride salt by treatment with ethereal hydrogen chloride followed by recrystallisation from methanol/ether then isopropanol, m.p. 172°–173°.

Analysis %: Found: C, 48.8; H, 8.8; N, 12.4. Calculated for $C_9H_{18}N_2O_2.HCl$: C, 48.5; H, 8.6; N, 12.6.

PREPARATION N

Preparation of 3-(N-n-butylcarbamoyl)piperidine

N-n-Butylnicotinamide (7.0 g) in acetic acid (100 ml) was hydrogenated over platinum oxide at 50° and 50 p.s.i. The catalyst was removed by filtration, the filtrate evaporated and the residue treated with toluene and evaporated in vacuo. The residue in chloroform (50 ml) was washed with sodium bicarbonate solution (3×50 ml) the organic layer separated, dried ($Na_2SO_4$) and the solvent evaporated in vacuo to give as an oil 3-(N-n-butylcarbamoyl)piperidine (3.8 g).

A sample in chloroform was converted to the oxalate salt by treatment with oxalic acid in ether, the resulting semi-solid triturated with ether and ethyl acetate then recrystallised from isopropanol, m.p. 145°–146°.

Analysis %: Found: C, 52.9; H, 8.4; N, 10.0. Calculated for $C_{10}H_{20}N_2O.C_2H_2O_4$: C, 52.5; H, 8.1; N, 10.2.

PREPARATION O

Preparation of 4-[N-(2,4-dimethoxybenzyl)carbamoyl]piperidine

1-Benzyloxycarbonyl-4-[N-2,4-dimethoxybenzylcarbamoyl]piperidine was prepared similarly to Preparation C starting from 1-benzyloxycarbonylpiperidine-4-carboxylic acid chloride and 2,4-dimethoxybenzylamine. The product was identified by n.m.r. spectroscopy. This product (7.6 g) in ethanol (150 ml) was hydrogenated over 5% palladium on charcoal at 50°/50 p.s.i. The catalyst was removed by filtration and the filtrate evaporated in vacuo to give 4-[N-(2,4-dimethoxybenzyl)carbamoyl]piperidine (5.0 g) as a solid. A sample in chloroform was converted to the hydrochloride salt by treatment with ethereal hydrogen chloride and recrystallised from isopropanol, m.p. 222°–224°.

Analysis %: Found: C, 57.4; H, 7.5; N, 8.9. Calculated for $C_{15}H_{22}N_2O_3.HCl$: C, 57.2; H, 7.4; N, 8.9.

PREPARATION P

Preparation of 4-amino-2-(4-carboxymethylpiperidino)-6,7-dimethoxyquinazoline hydrochloride 4-Amino-2-chloro-6,7-dimethoxyquinazoline (17.3 g), piperidine-4-acetic acid hydrochloride (12.0 g) and triethylamine (20 ml) in n-butanol (500 ml) were stirred under reflux for 20 hours. The mixture was then cooled to 0°–4° and the separated product collected. The solid was slurried with acetone (100 ml), filtered, slurried with chloroform (100 ml), filtered and washed with ether to give 4-amino-2-(4-carboxymethylpiperidino)-6,7-dimethoxyquinazoline hydrochloride (19.0 g). A sample was recrystallised from acetic acid and had an m.p. of 250°–252°.

Analysis %: Found: C, 53.1; H, 6.4; N, 14.2. Calculated for $C_{17}H_{22}N_4O_4.HCl$: C, 53.3; H, 6.1; N, 14.6.

PREPARATION Q

Preparation of 4-Amino-2-[4-(2-carboxyethyl)piperidino]-6,7-dimethoxyquinazoline hydrochloride 4-Amino-2-chloro-6,7-dimethoxyquinazoline (24.9 g) and 3-(4-piperidinyl)propionic acid, hydrochloride (20 g) in n-butanol (1000 ml) were stirred under reflux for 20 hours. The hot suspension was filtered and the insoluble material discarded. The filtrate was cooled in ice/water, the precipitated solid collected and the filtrate evaporated in vacuo. The resulting solid and the precipitated solid were combined and crystallised from isopropanol to give 4-amino-2-[4-(2-{n-butoxycarbonyl}ethyl)piperidino]-6,7-dimethoxyquinazoline, hydrochloride (27.0 g) with m.p. 250°–252°.

Analysis %: Found: C, 58.0; H, 7.3; N, 12.5. Calculated for $C_{22}H_{32}N_4O_4.HCl$: C, 58.3; H, 7.3; N, 12.4.

This n-butyl ester (20 g) in methanol (50 ml) and sodium hydroxide solution (50 ml, 5 N) was heated under reflux for 4 hours. The organic solvent was evaporated and the aqueous residue acidified with 2 N hydrochloric acid, and cooled. The precipitated solid was collected, dried, slurried with ether and filtered to give 4-amino-2-[4-(2-carboxyethyl)piperidino]-6,7-dimethoxyquinazoline, hydrochloride (17.9 g). A sample was recrystallised from water followed by DMF and had an m.p. of 238°–241°.

Analysis %: Found: C, 54.2; H, 6.3; N, 14.3. Calculated for $C_{18}H_{24}N_4O_4.HCl$: C, 54.5; H, 6.4; N, 14.1

PREPARATION R

A. Preparation of ethyl 2-(1-Acetyl-piperidin-4-oxy)phenylacetate

N-Acetyl-4-hydroxypiperidine (27.5 g) in dry DMF (100 ml) was added slowly to a stirred suspension of sodium hydride (25 g, 50% dispersion in mineral oil) in DMF (150 ml) and dimethoxyethane (10 ml). The suspension was stirred at room temperature for 3 hours. 2-Bromophenylacetic acid (45 g) in DMF (250 ml) was then added slowly with ice/water cooling. The mixture was stirred at room temperature for 20 hours, then isopropanol added and the solvent evaporated in vacuo. The residue was taken up in water, acidified to pH 1 with 2 N hydrochloric acid and extracted four times with chloroform (300 ml).

The combined chloroform extracts were washed with water and brine, dried ($MgSO_4$) and the solvent evaporated in vacuo. The residue in anhydrous ethanol (450 ml) with concentrated sulphuric acid (9 ml) was heated under reflux for 8 hours. The cooled solution was cautiously neutralised with aqueous sodium carbonate solution and the organic solvent evaporated in vacuo. The aqueous residue was adjusted to pH 10 with sodium carbonate solution and extracted twice with chloroform. The combined chloroform extracts were dried (MgSO$_4$), and evaporated in vacuo. Distillation of the residue gave ethyl 2-(1-acetyl-piperidin-4-oxy)phenylacetate (37.2 g), b.p. 190°–194°/0.18 mm.

Analysis %: Found: C, 66.4; H, 7.8; N, 4.5. Calculated for $C_{17}H_{23}NO_4$: C, 66.9; H, 7.6; N, 4.6.

B. Preparation of 2-[piperidin-4-oxy]phenylacetic acid, hydrochloride

Ethyl 2-[1-acetylpiperidin-4-oxy]phenylacetate (10.0 g) in methanol (50 ml) and sodium hydroxide solution (30 ml, 5 N) was heated under reflux for 5 hours. The organic solvent was evaporated in vacuo and the aqueous residue was acidified to pH 2 with hydrochloric acid solution and filtered. The filtrate was evaporated in vacuo, treated with toluene and evaporated in vacuo. The residue was treated with isopropanol (50 ml), filtered and the solid washed with isopropanol. The filtrate and washings were combined and the solvent evaporated in vacuo. The residue was triturated with acetone, the white solid collected and crystallised from isopropanol to give 2-(piperidin-4-oxy)phenylacetic acid, hydrochloride, m.p. 180°–182° (5.05 g).

Analysis %: Found: C, 57.4; H, 6.8; N, 5.5. Calculated for $C_{13}H_{17}NO_3.HCl$: C, 57.5; H, 6.7; N, 5.2.

C. Preparation of 4-amino-2-[4-(1-carboxy-1-phenyl-methoxy)-piperidino]-6,7-dimethoxyquinazoline 4-Amino-2-chloro-6,7-dimethoxyquinazoline (4.8 g), 2-(piperidin-4-oxy)phenylacetic acid hydrochloride (4.9 g) and triethylamine (5 ml) in n-butanol (100 ml) were heated under reflux for 20 hours. The mixture was cooled, and the precipitated solid was collected and washed with ether. A sample of this solid (0.7 g) was recrystallised from acetic acid, and the resulting solid washed with ether to give 4-amino-2-[4-(1-carboxy-1-phenyl-methoxy)piperidino]-6,7-dimethoxyquinazoline, acetate (0.56 g), m.p. 271°–274°.

Analysis %: Found: C, 60.0; H, 6.0; N, 11.3. Calculated for $C_{23}H_{26}N_4O_5.CH_3CO_2H$: C, 60.2; H, 6.1; N, 11.2.

The remaining product was slurried with hot isopropanol, filtered and the solid washed with isopropanol and ether to give 4-amino-2-[4-(1-carboxy-1-phenyl-methoxy)piperidino]-6,7-dimethoxy quinazoline (6.46 g).

PREPARATION S

Preparation of Mono-N-(methanesulphonyl)ethylene diamine

Methanesulphonyl chloride (16.8 g) in dry chloroform (25 ml) was added dropwise to a stirred solution of mono-N-acetylethylene diamine (15 g) and triethylamine (15 ml) in dry chloroform (25 ml) at 0°. The solution was stirred at ambient temperature for 60 hours. The reaction mixture was then extracted with water (3×50 ml) and the combined aqueous fractions were shaken with chloroform and separated. The aqueous fraction was evaporated in vacuo and the residue in methanol (100 ml) and concentrated hydrochloric acid (50 ml) was heated under reflux for 12 hours. The solvent was then evaporated in vacuo and the residue treated with methanol at reflux. The insoluble solid was filtered off and discarded. The filtrate was evaporated in vacuo and the residue treated with chloroform at reflux. The solvent was decanted leaving N-monomethanesulphonylethylene diamine, hydrochloride as a semi-solid also containing triethylamine hydrochloride. The product was used in the preparation of the product of Example 36 without further purification.

PREPARATION T

A. Preparation of Methyl Ester of 3-(piperid-4-yl) propionic acid

Diethyl malonate (50 g.), 4-pyridylaldehyde (30 g.) and 1-methylpiperazine (4 ml.) were heated overnight under reflux in toluene (200 ml.), utilizing a Dean and Stark water trap. The toluene was then removed in vacuo and the residue distilled to give ethyl 2-ethoxycarbonyl-3-(pyrid-4-yl) acrylate, b.p. 140°–150°/1.5 mm., (35 g.). Hydrogenation of this in glacial acetic acid (600 ml.) over platinum oxide at 60°/60 p.s.i. until hydrogen uptake ceased gave, after removal of catalyst and solvent, the crude acetate salt of diethyl 2-(piperid-4-yl) malonate, which was then heated overnight, under reflux, with concentrated hydrochloric acid (500 ml.) to give, on evaporation to dryness, 3-(piperid-4-yl) propionic acid hydrochloride.

Conversion to the methyl ester was achieved by dissolving the crude acid hydrochloride in methyl alcohol (600 ml.), and adding thionyl chloride (200 ml.) cautiously, dropwise. On completion of the addition the mixture was heated under reflux for 3½ hours, evaporated to dryness, basified with 2 N sodium hydroxide (to pH 12), and extracted with chloroform (2×100 ml.). The crude ester was obtained by evaporation of the dried chloroform extract. (Yield of methyl ester=14 g.).

B. Preparation of N-n-Propyl-2-(piperid-4-yl)acetamide

Methyl 2-(pyrid-4-yl)acetate (10 g.), n-propylamine (30 ml.) and 3 A molecular sieves (10 g.) were heated together at 100° for 148 hours in a stainless steel bomb. Excess amine and molecular sieves were removed and the crude product in glacial acetic acid (100 ml.) was hydrogenated over platinum oxide catalyst at 30°/50 p.s.i. until uptake of hydrogen ceased. The catalyst was removed by filtration, the excess acetic acid distilled off in vacuo, and the residue basified with aqueous sodium bicarbonate and extracted with ethyl acetate (100 ml.). The organic layer was dried (MgSO$_4$) and evaporated in vacuo to give crude N-n-propyl-2-(piperid-4-yl) acetamide as an oil. This was utilized without further purification.

[It should be noted that 4-amino-2-chloro-6,7-dimethoxyquinazoline and the substituted piperidine intermediates used in Examples 3,8 and 9 are known compounds as are the amines used in Example 19 onwards (apart from the amine used in Example 36, whose preparation is described above) are known compounds].

We claim:
1. Compounds having the general formula:

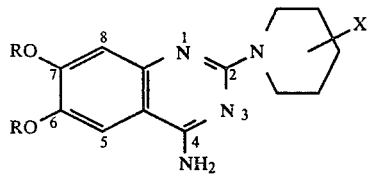

wherein

R is lower alkyl;

X, which is attached to the 3- or 4- position of the piperidino group, is selected from the group consisting of —(CH$_2$)$_n$CONR$^1$R$^2$, —O(CH$_2$)$_n$CONR$^1$R$^2$ and

—OCHCONR$^1$R$^2$;

wherein n is 0 or an integer from 1 to 2;

R$^1$ is selected from the group consisting of hydrogen and lower alkyl;

R$^2$ is selected from the group consisting of phenyl, mono-lower alkylphenyl, mono- and di-lower alkoxy phenyl, mono- and di-chlorophenyl, C$_{3-7}$ cycloalkyl, lower alkenyl, lower alkynyl, lower alkyl and mono-substituted lower alkyl wherein the substitutent is selected from the group consisting of C$_{3-7}$ cycloalkyl, hydroxy, lower alkoxy, lower alkoxy carbonyl, phenyl, mono-lower alkylphenyl, mono- and di-lower alkoxyphenyl, mono- and di-chlorophenyl, phenoxy, chloro and NR$^3$R$^4$ wherein R$^3$ is selected from the group consisting of hydrogen and lower alkyl and R$^4$ is selected from the group consisting of lower alkyl, lower alkanoyl and lower alkylsulfonyl; with the proviso that any O, N or chloro atom in R$^2$ is separated by at least two carbon atoms from the nitrogen atom to which R$^2$ is attached;

R$^1$ and R$^2$ taken together with the nitrogen atom to which they are attached are selected from the group consisting of morpholino, 1,2,3,4-tetrahydroisoquinolyl and mono- and dimethoxy substituted 1,2,3,4-tetrahydroisoquinolyl;

and the pharmaceutically acceptable acid addition salts thereof.

2. A compound according to claim 1 wherein R is methyl; X is attached to the 4- position of the piperidino group and is selected from the group consisting of:

(a) —CONR$^1$R$^2$ wherein R$^1$ is selected from the group consisting of hydrogen, methyl and ethyl; R$^2$ is selected from the group consisting of C$_{3-6}$ cycloalkyl; 2-propenyl, 2-methyl-2-propenyl, propargyl, phenyl, C$_{1-6}$ alkyl, and substituted C$_{1-2}$ alkyl wherein the substituent is selected from the group consisting of phenyl, mono-methylphenyl, mono- and di-(C$_{1-2}$ alkoxy)phenyl, mono- and di-chlorophenyl, hydroxy, C$_{1-2}$ alkoxy, (C$_{1-2}$ alkoxy)-carbonyl, phenoxy, —N(CH$_3$)$_2$, —NHCOCH$_3$, —NHSO$_2$CH$_3$, chloro and C$_{3-6}$ cycloalkyl; with the proviso that any O, N or chloro atom in R$^2$ is separated by at least 2 carbon atoms from the nitrogen atom to which R$^2$ is attached; R$^1$ and R$^2$ taken together with the nitrogen atom to which they are attached are selected from the group consisting of 1,2,3,4-tetrahydroisoquinolyl, dimethoxy substituted 1,2,3,4-tetrahydroisoquinolyl and morpholino;

(b) —CH$_2$CONHR$^2$ wherein R$^2$ is selected from the group consisting of C$_1$-C$_4$ alkyl, benzyl, cyclopropylmethyl and —CH$_2$CH=CH$_2$;

(c) —CH$_2$CH$_2$CONHR$^2$ wherein R$^2$ is selected from the group consisting of C$_1$-C$_4$ alkyl and benzyl;

(d) —O(CH$_2$)$_n$CONH(C$_1$-C$_6$ alkyl) wherein n is 0 or 1; and (e)

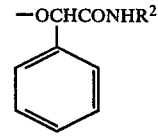

—OCHCONHR$^2$ wherein R$^2$ is selected from the group consisting of C$_{1-4}$alkyl, benzyl and cyclopropylmethyl.

3. A compound according to claim 2 wherein R is methyl; X is selected from the group consisting of:

—(CH$_2$)$_n$CONR$^1$R$^2$ and —O(CH$_2$)$_n$CONR$^1$R$^2$ wherein R$^1$ is hydrogen; R$^2$ is selected from the group consisting of C$_{1-4}$ alkyl, C$_{3-6}$ cycloalkylmethyl, benzyl and 2-propenyl; and n is 0 or 1.

4. A compound according to claim 3 wherein n is 0.

5. A compound according to claim 3 wherein n is 1.

6. A compound according to claim 4 wherein R$^2$ is C$_{1-4}$ alkyl.

7. The compound according to claim 6 wherein R$^2$ is ethyl.

8. The compound according to claim 5 wherein R$^2$ is n-propyl.

9. A pharmaceutical composition comprising antihypertensive amount of a compound of claim 1 or a pharmaceutically acceptable acid addition salt thereof, together with a pharmaceutically acceptable diluent or carrier.

10. A method for the treatment of hypertension which comprises administering to a hypertensive host, an antihypertensive effective amount of a compound according to claim 1.

* * * * *